United States Patent
Sassone-Corsi

(10) Patent No.: US 6,660,841 B1
(45) Date of Patent: *Dec. 9, 2003

(54) ACTIVATOR OF CREM IN TESTIS AND ITS USES

(75) Inventor: Paolo Sassone-Corsi, Strasbourg (FR)

(73) Assignee: Association pour le Developpement de la Recherche en Genetique Moleculaire (ADEREGEM), Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 09/522,689

(22) Filed: Mar. 10, 2000

Related U.S. Application Data

(60) Provisional application No. 60/123,744, filed on Mar. 10, 1999.

(51) Int. Cl.⁷ .................... C07K 14/435; C07K 14/00; C12N 15/12; C12N 15/62; C12N 15/85
(52) U.S. Cl. .................... 530/350; 435/69.1; 435/69.7; 435/252.3; 435/320.1; 536/23.5
(58) Field of Search .................. 530/350; 435/69.1, 435/252.3, 320.1, 69.7; 536/23.5

(56) References Cited

FOREIGN PATENT DOCUMENTS

WO          WO 00/14231 A1   *   3/2000

OTHER PUBLICATIONS

Fimia, G.M., et al., 1999, "CBP–independent activation of CREM and CREB by the LIM–only protein ACT", Nature, vol. 398, pp. 165–169.*

EST database Accession No. AA824347, 1998, "*Homo sapiens* cDNA clone 1391847 3'–similar to . . . LIM Protein 3", 579bp, National Cancer Institute, Cancer Genome Anatomy Project, Tumor Gene Index, I.M.A.G.E. Consortium/LLNL.*

Chan, K.K., et al., 1998, "Molecular cloning and characterization of FHL2, a novel LIM domain protein preferentially expressed in human heart", Gene, vol. 210, pp. 345–350.*

Marc Montminy, "Transcriptional Regulation By Cyclic AMP", Annual Review of Biochemistry, vol. 66, pp. 807–822, 1997.

Paolo Sassone–Corsi, "Transcription Factors Responsive to cAMP", Annual Review of Cellular Development, Biochemistry, vo. 11, pp. 355–377, 1995.

Paolo Sassone–Corsi, "Transcriptional Checkpoints Determining the Fate of Male Germ Cells", Cell, vol. 88, pp. 163–166, 1997.

Nicholas Fouldes et al., "Developmental switch of CREM function during spermatogenesis: from antagonist to activator", Letters to Nature, vol. 355, pp. 80–84, 1992.

K. Ferreri et al., "The cAMP–regulated transcription factor CREB interacts with a component of the TFIID complex", Proceedings of the National Academy of Science, vol. 91, pp. 1210–1213, 1994.

Francois Nantel et al., "Spermiogenesis deficiency and germ–cell apoptosis in CREM–mutant mice", Letters to Nature, vol. 380, pp. 159–162, 1996.

(List continued on next page.)

*Primary Examiner*—Tekchand Saidha
*Assistant Examiner*—William W. Moore
(74) *Attorney, Agent, or Firm*—Foley & Lardner

(57) ABSTRACT

The present invention deals with a protein activation of CREM in Testis named ACT, the cDNA encoding ACT and a method to select compounds which are able to interact with ACT or its site of interaction on CREM to block or stimulate the CREM transcriptional activity in Testis. Such compounds may be useful to control male fertility.

11 Claims, 9 Drawing Sheets

Figure 1B:
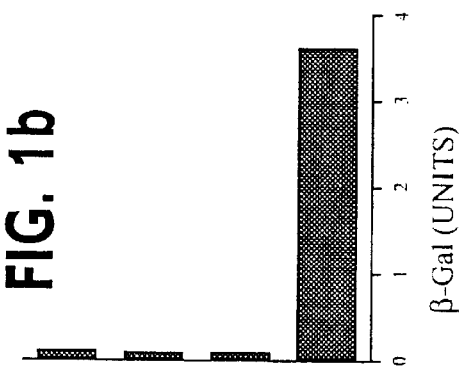

```
  1  MTSSQFDCQY CTSSLIGKKY VLKDDNLYCI SCYDRIFSNY CEQCKEPIES

51  DSKDLCYKNR HWHEGCFRCN KCHHSLVEKP FVAKDDRLLC TDCYSNECSS

101  KCFHCKRTIM PGSRKMEFKG NYWHETCFVC EHCRQPIGTK PLISKESGNY

151  CVPCFEKEFA HYCNFCKKVI TSGGITFRDQ IWHKECFLCS GCRKELYEEA

201  FMSKDDFPFC LDCYNHLYAK KCAACTKPIT GLRGAKFICF QDRQWHSECF

251  NCGKCSVSLV GEGFLTHNME ILCRKCGSGA DTDA
```

OTHER PUBLICATIONS

Julie A. Blendy et al., "Severe impairment of spermatogenesis in mice lacking the CREM gene", Letters to Nature, vol. 380, pp. 162–165, 1996.

Igor B. Dawid et al., "LIM domains: multiple roles as adapters and functional modifiers in protein interactions", Trends in Genetics, vol. 14, No. 4, pp. 156–162, 1998.

Jennifer Curtiss et al., "DeLIMiting development", BioEssays, vol. 20, pp. 58–69, 1998.

Veronique Delmas et al., "Induction of CREM activator proteins in spermatids: down–stream targets and implications for haploid germ cell differentiation", Molecular Endocronology, vol. 7, pp. 1502–1514, 1993.

Carlos A. Molina et al., "Inducibility and Negative Autoregulation of CREM: An Alternative Promoter Directs the Expression of ICER, An Early Response Repressor", Cell, vol. 75, pp. 875–886, 1993.

Brid M. Laoide et al.,"The functional versatility of CREM is determined by its modular structure", The EMBO Journal, vol. 12, No. 3, pp. 1179–1191, 1993.

Marian A. Martinez–Balbas et al., "The acetyltransferase of CBP stimulates transcription", The EMBO Journal, vol. 17, No. 10, pp. 2886–2893, 1998.

Yudong Zhou et al., "cAMP–response element modulator is a positive regulator of testis angiotensin converting enzyme transcription", Proceedings of the National Academy of the National Academy of Science, vol. 993, pp. 12262–12266, 1996.

Zuoming Sun et al., "Calspermin Gene Transcription is Regulated by Two Cyclic AMP Response Elements Contained in an Alternative Promoter in the Calmodulin Kinase IV Gene", Molecular and Cellular Biology, vol. 15, pp. 561–571, 1995.

Markus Künzler et al., "Functional differences between mammalian transcription activation domains at the yeast GAL 1 promoter", the EMBO Journal, vol. 13, No. 3, pp. 641–645, 1994.

John C. Chrivia et al., "Phosphorylated CREB binds specifically to the nuclear protein CBP", Letters to Nature, vol. 365, pp. 855–859, 1993.

Roland P.S. Kwok et al., "Nuclear protein CBO is a coactivator for the transcription factor CREB", Letters to Nature, vol. 370, pp. 223–226, 1994.

J. Arias et al., "Activation of cAMP and mitogen responsive genes relies on a common nuclear factor", Letters to Nature, vol. 370, pp. 226–229, 1994.

Rolf P. de Groot et al., "Multiple and cooperative phosphorylation events regulate the CREM activator function", The EMBO Journal, vol. 12, No. 10, pp. 3903–3911, 1993.

Gustavo A. Gonzalez et al., "Cyclic AMP Stimulates Somatostatin Gene Transcription by Phosphorylation of CREB at Serine 133", Cell, vol. 59, 675–680, 1989.

V. E. Valge–Archer et al., "The LIM protein RBTN2 and the basic helix–loop–helix protein TAL1 are present in a complex in erythroid cells", Proceedings of the National Academy of Science, vol. 91, pp. 8617–8621, 1994.

Isobel Wadman et al., "Specific in vivo association between the bHLH and LIM proteins implicated in human T cell leukemia", The EMBO Journal vol. 13, No. 20, pp. 4831–4839, 1994.

H. Osada et al., "Association of erythroid transcription factors: complexes involving the LIM protein RBTN2 and the zinc–finger protein GATA1", Proceedings of the National Academy of Science, vol. 92, pp. 9585–9589, 1995.

Yanfeng Kong et al., "Muscle LIM Protein Promotes Myogenesis by Enhancing the Activity of MyoD", Molecular and Cellular Biology, vol. 17, 4750–4760, 1997.

Morgan Sheng et al., "CREB: A $ca^{2+}$–Regulated Transcription Factor Phosphorylated by Calmodulin–Dependent Kinases", Science, vol. 252, pp. 1427–1430,1991.

Piotr Chomczynski et al., "Single–Step Method of RNA isolation by Acid Guanidinium Thiocyanate–Phenol–Chloroform Extraction", Analytical Biochemistry, vol. 162, pp. 156–159, 1987.

Nicholas S. Foulkes et al., "CREM Gene: Use of Alternative DNA–Binding Domains Generates Multiple Antagonists of cAMP–Induced Transcription", Cell, vol. 64, pp. 739–749, 1991.

Stephen Green et al., "A versatile in vivo and in vitro eukaryotic expression vector for protein engineering", Nucleic Acids Research, vol. 16, No. 1, 369, 1988.

Ralph A. W. Rupp et al., "Xenopus embryos regulate the nuclear localization of XmyoD", Genes and Development, vol. 8, pp. 1311–1323, 1994.

* cited by examiner

```
1    MTSSQFDCQY CTSSLIGKKY VLKDDNLYCI SCYDRIFSNY CEQCKEPIES
51   DSKDLCYKNR HWHEGCFRCN KCHHSLVEKP FVAKDDRLLC TDCYSNECSS
101  KCFHCKRTIM PGSRKMEFKG NYWHETCFVC EHCRQPIGTK PLISKESGNY
151  CVPCFEKEFA HYCNFCKKVI TSGGITFRDQ IWHKECFLCS GCRKELYEEA
201  FMSKDDFPFC LDCYNHLYAK KCAACTKPIT GLRGAKFICF QDRQWHSECF
251  NCGKCSVSLV GEGFLTHNME ILCRKGSGA DTDA
```

G4CREM    −   +   −   −   +   −
G4CREM117   −   −   +   −   −   +
Myc-ACT    −   −   −   +   +   +

Western CREM

Western Myc

IP Gal4

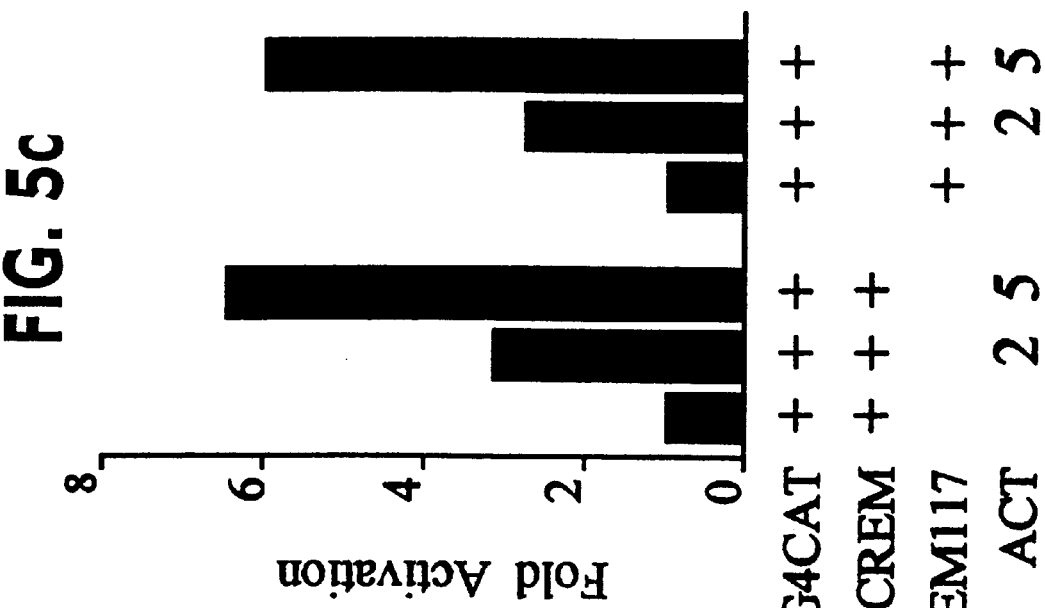
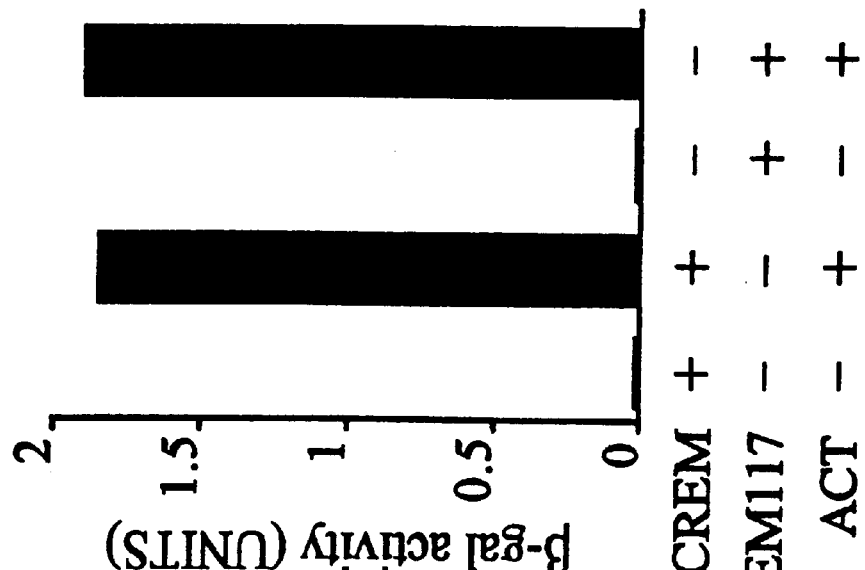

ACTIVATOR OF CREM IN TESTIS AND ITS USES

This is a Continuation-in-Part of Application No. 60/123,744 filed on Mar. 10, 1999.

The present invention deals with a new protein activator of CREM in Testis named ACT, the cDNA encoding ACT and the use of said protein and cDNA for screening modulating compounds which are able to interact with ACT or its site of interaction on CREM to block or stimulate the CREM transcriptional activity in Testis. Such compounds may lead to control of male fertility.

Transcriptional activation by CREB and CREM requires serine phosphorylation within the activation domain (Ser133 in CREB; Ser117 in CREM) and consequent interaction with the co-activator CBP[1,2]. The activator CREM is expressed at very high levels in male germ cells and is required for post-meiotic gene expression[2-4]. Using a two-hybrid screen, we have isolated a testis-derived cDNA encoding ACT (Activator of CREM in Testis), a novel LIM-only protein that specifically associates with CREM. ACT is expressed coordinately with CREM in a highly tissue- and developmentally-regulated manner. ACT powerfully stimulates CREM transcriptional activity in yeast and mammalian cells and it contains an intrinsic activation function. Strikingly, ACT bypasses the classical requirements for activation, namely Ser117-phosphorylation and interaction with CBP. Thus, ACT identifies a novel pathway of transcriptional activation by CREM and CREB. ACT may define a novel class of tissue-specific co-activators whose function could be specific of distinct cellular differentiation programs.

CREB and CREM are factors directly coupled to signaling pathways. Phosphorylation within the P-box, and consequent CBP interaction, turns them into powerful activators[1,2]. The activation domain (AD) comprises also two glutamine-rich regions Q1 and Q2 interaction to the TBP-associated hTAF130 seems involved in activation[5]. While CREB is ubiquitous, CREM displays a remarkable tissue distribution and plays important roles in the nuclear response to physiological stimuli[2]. In particular, the activator CREM is hundred-fold more abundant in male germ cells than in any other tissue[4]. CREM controls the transcription of various post-meiotic genes[2,3] and its targeted inactivation in the mouse results in the complete block of spermatogenesis at early spermatids stage[6,7]. Unexpected recent results show that the activator CREM is not phosphorylated at Ser117 in germ cells (in preparation). Thus, while the physiological role of CREM in germ cells is well established, the molecular mechanism by which it exerts its function remains elusive.

Figure 1A:
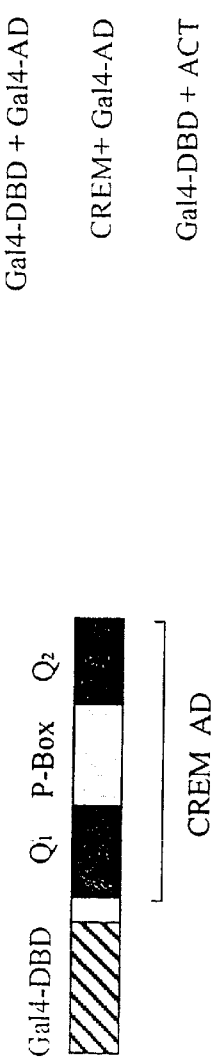
Figure 1C:
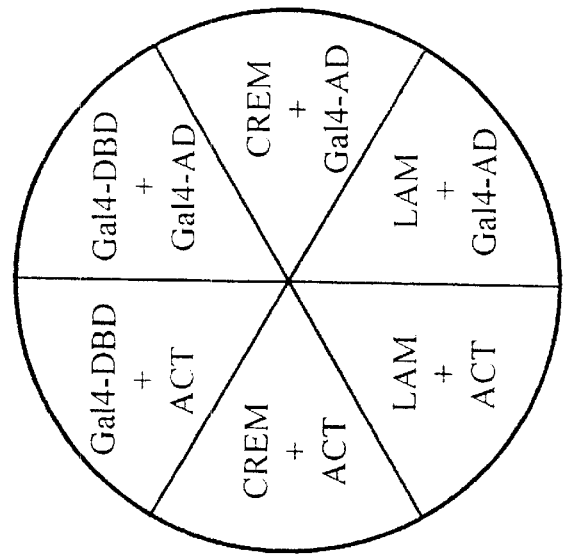
Figure 1C:
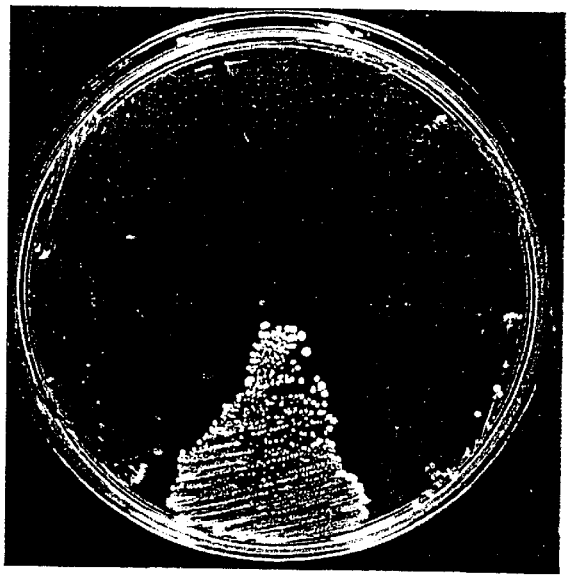
Figure 1C:
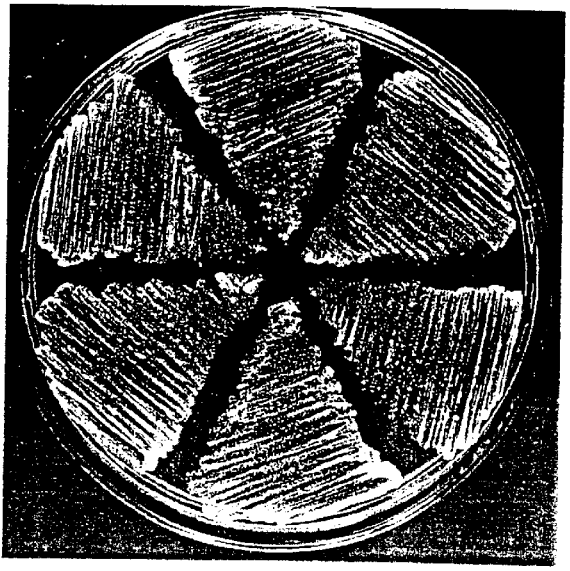
Figure 1D:
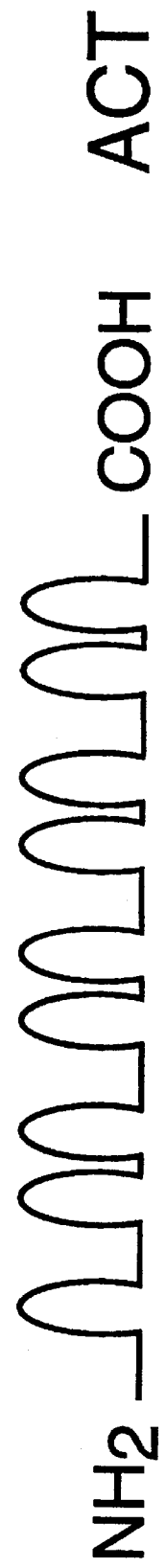

We wished to investigate how activation by CREM could occur in the absence of phosphorylation. A yeast two-hybrid was used to screen a murine testis cDNA expression library with the CREM AD (FIG. 1a). The CREM AD fused to the GAL4 DBD (DNA-binding domain) is completely inactive (FIGS. 1b; 1c) for the lack of CBP and hTAF130 yeast homologs. One clone interacted with high affinity when tested for nutritional selection and β-galactosidase activity (FIGS. 1b; 1c). This encodes a novel 284aa protein (SEQ ID NO:1) FIG. 1d) ACT (activator of CREM in testis), containing four complete and one N-terminal half LIM motif (FIG. 1d). LIM domains are constituted by double zinc-finger structures, are present in various proteins and thought to mediate protein-protein interactions[8,9].

Figure 2B:
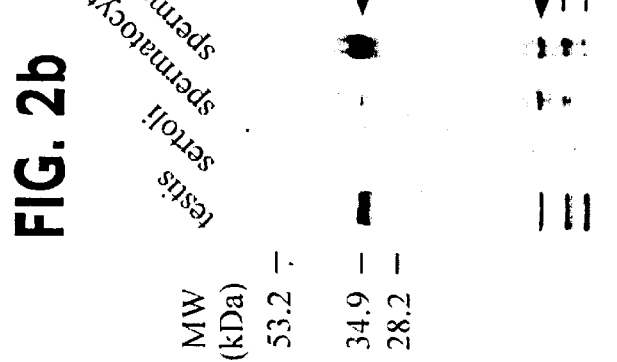
Figure 2A:
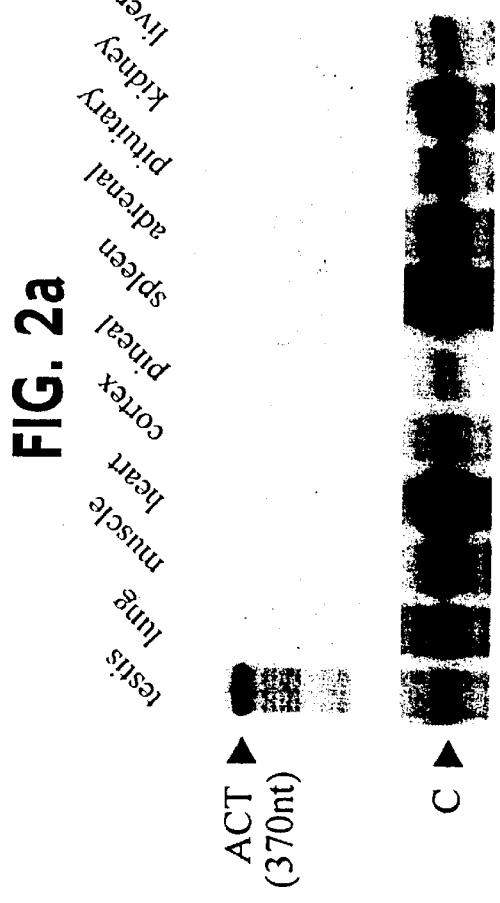
Figure 2D:
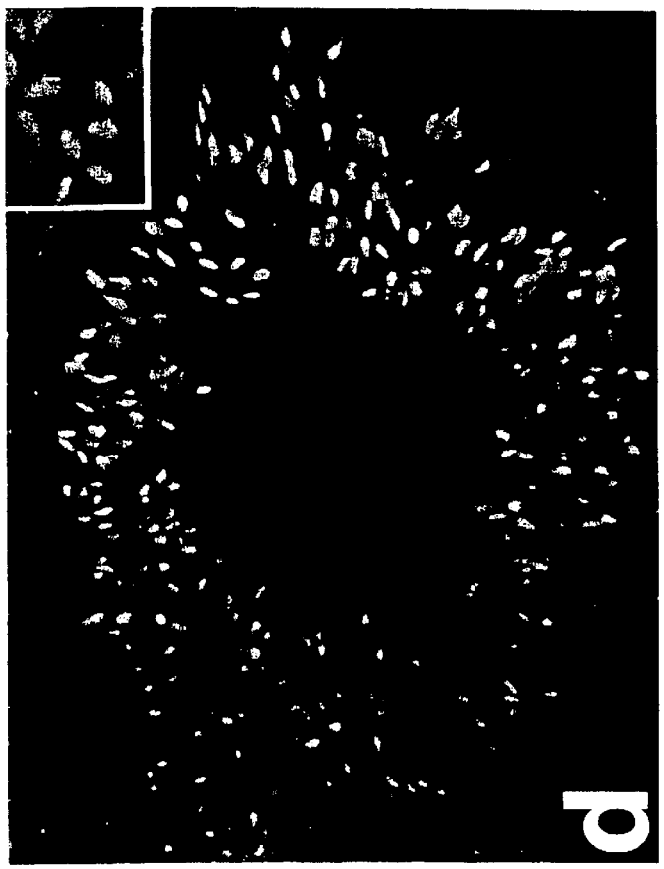
Figure 2C:
Figure 3A:
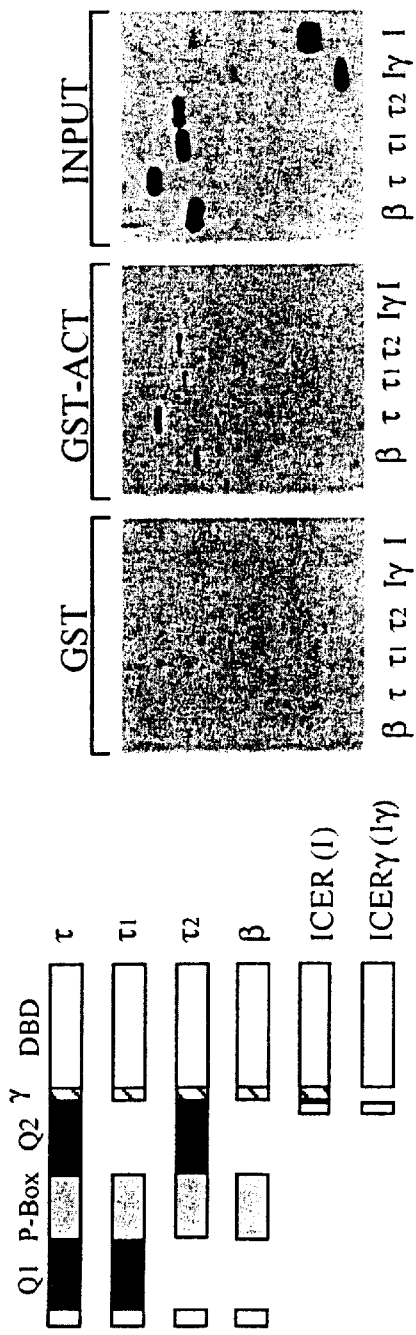
Figure 3B:
Figure 3D:
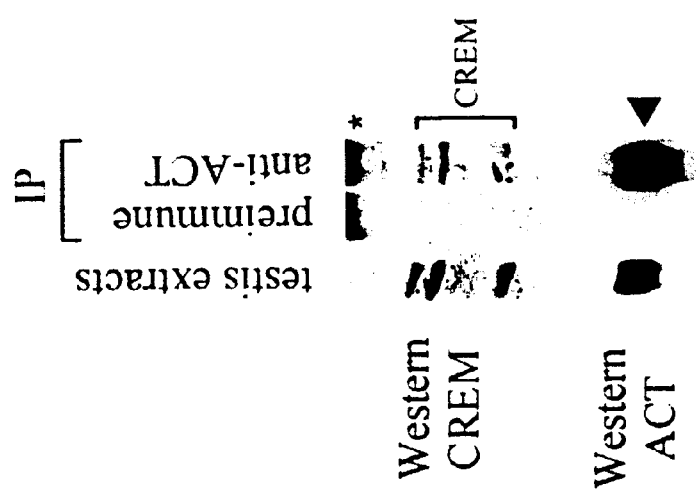
Figure 3C:
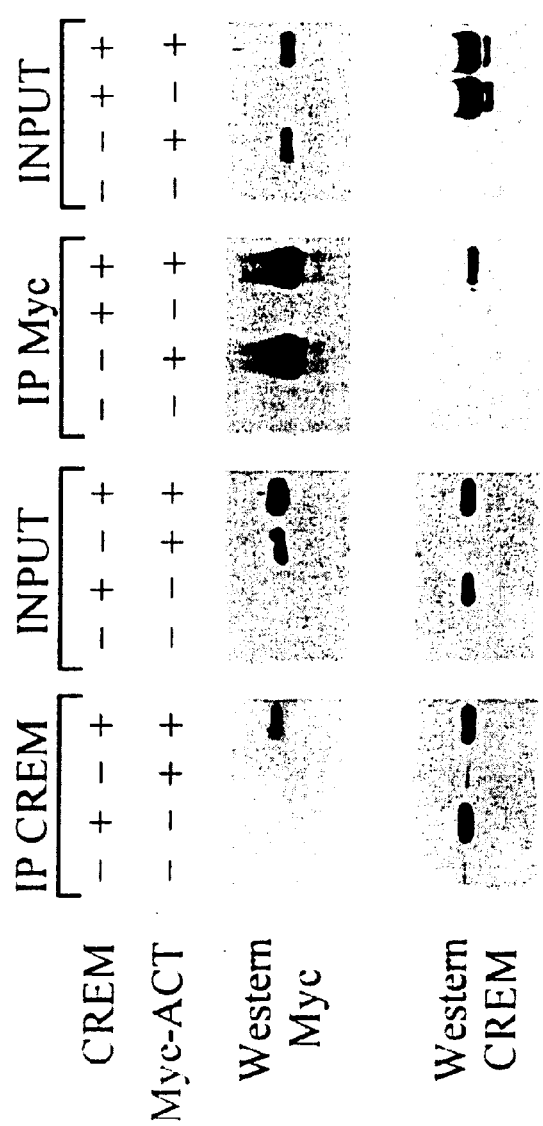

ACT displays a remarkable tissue-specific expression (FIG. 2a). We have raised anti-ACT specific antibody which revealed a protein of the expected size (33 kDa). ACT protein colocalizes in purified spermatids with CREM[10] (FIG. 2b). In situ analysis shows regulated expression during germ cell differentiation (FIG. 2c), coordinated with CREM[10]. Immunohistochemistry demonstrates that ACT is nuclear and expressed in round and elongated spermatids (FIG. 2d). Thus, CREM and ACT proteins are coexpressed in vivo.

ACT and CREM proteins efficiently associate (FIG. 3). Purified full-length ACT fused to glutathione-S-transferase (GST) was tested for binding to different CREM isoforms. The presence of the sole P-box is sufficient for binding ACT (FIG. 3a). Consistent with the yeast two-hybrid assay, ACT does not bind to the repressor ICER[11], indicating that the DBD is dispensable for interaction. To map the region involved in CREM association, we generated ACT truncations in each LIM motif. Mutants lacking the fourth LIM domain (GST-ACT 1–221) or the N-terminal half LIM domain (GST-ACT 38–284) interact with CREM, while deletion of the two C-terminal LIM domains (GST-ACT 1–162) impairs association (FIG. 3b). Thus, the third LIM domain appears critical for CREM-ACT interaction. CREM-ACT association is also revealed by co-immunoprecipitation after expression in mammalian cells (FIG. 3c). Extracts from cells transfected with CREM and Myc-tagged ACT expression vectors, individually or in combination, were immunoprecipitated using anti-CREM antibodies. Western analysis (FIG. 3c) revealed that ACT associates with CREM in immunoprecipitated complexes. No ACT protein was co-immunoprecipitated by anti-CREM antibodies when ACT and CREM were expressed separately. Conversely, CREM-ACT association was detected when the Myc-tagged ACT protein was immunoprecipitated from co-transfected cells, using an anti-Myc antibody (FIG. 3c). Finally, the CREM-ACT association is also revealed by co-immunoprecipitation of native proteins from a testis extract (FIG. 3d).

Figure 4A:
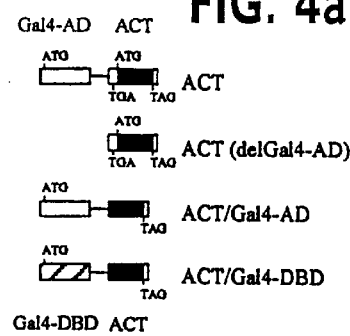
Figure 4A:
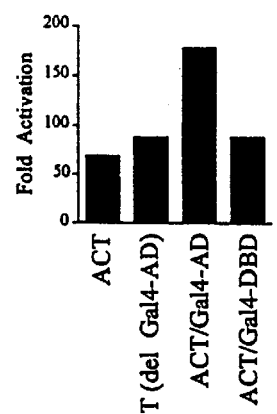

Sequence analysis of the ACT cDNA from the two-hybrid screening held a surprise: the coding sequence was not in frame with the GAL4 AD within the yeast expression vector. Thus ACT could be translated from its own AUG and therefore have intrinsic coactivator properties in yeast. To test this, the GAL4-AD was deleted generating ACT (delGal4-AD) (FIG. 4a). Strikingly, ACT alone powerfully activates CREM-dependent transcription. Thus ACT bypasses the requirement of CBP for activation, as CBP is lacking in yeast. A fusion of ACT in frame with GAL4 AD (ACT/Gal4-AD) elicits only a two-fold higher activity than ACT, indicating that ACT, per se, has an efficient activation potential. To assess whether ACT has an intrinsic AD we fused it to the GAL4 DBD (ACT/Gal4-DBD). This fusion protein efficiently induces activation (FIG. 4a). Thus, ACT bears an autonomous AD as its recruitment to DNA is sufficient to elicit activation.

Figure 4B:
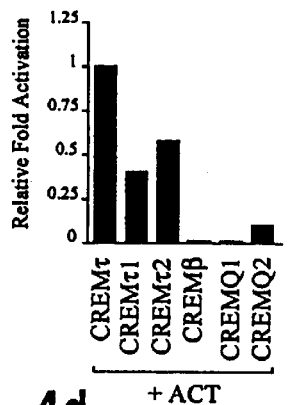

The CREM gene generates both activators and repressors[2,12]. Is ACT able to modify the repressors function? In a two-hybrid assay ACT-mediated co-activation takes place only in the presence of CREM activator isoforms, as the P-box in combination with at least one glutamine-rich domain is required (CREMτ1 and CREMτ2, FIG. 4b).

Figure 4C:
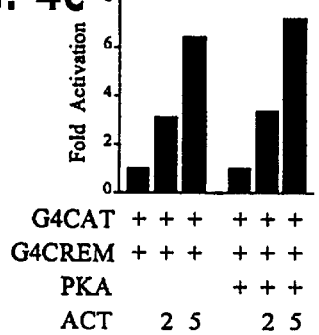
Figure 4D:
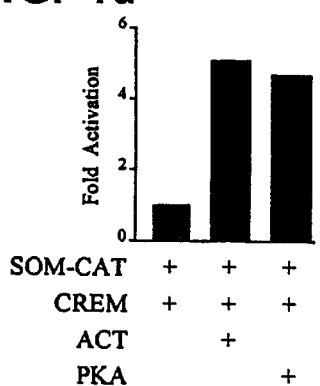
Figure 4E:
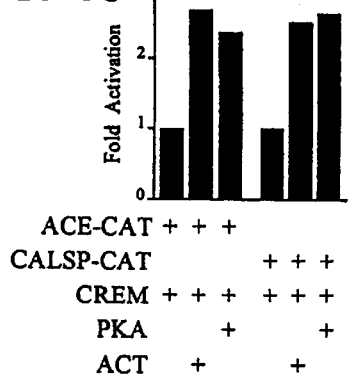
Figure 4F:
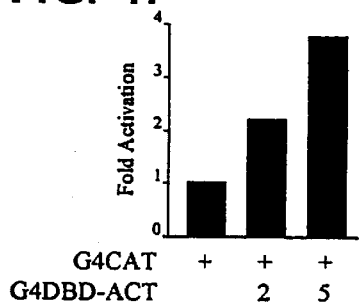

ACT is a powerful activator in mammalian cells. Using a GAL4-based reporter[13] CREM-mediated activation was enhanced by ACT in a dose-dependent manner. Strikingly, ACT functions in absence of co-expressed PKA catalytic subunit (FIG. 4c). Analogous results were obtained with full-length CREM and CREB on a CRE-driven somatostatin reporter and the testis-specific angiotensin converting enzyme (ACE) and calspermin promoters[14,15] (FIG. 4d,e; not shown). ACT displays inherent activating function also in mammalian cells, as ACT fused to the GAL4 DBD strongly stimulates transcription from the G4CAT reporter (FIG. 4f).

Figure 4G:
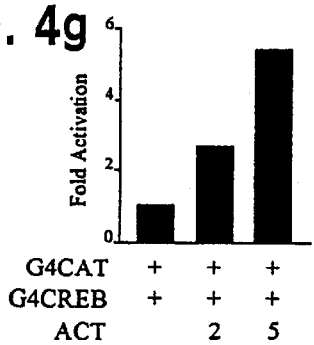

We wished to test ACT function on CREB, as it is known that GAL4 DBD fusion proteins containing the glutamine-rich activation domains are inactive in yeast[16]. We show that ACT significantly activates CREB-mediated transcription both in yeast and in mammalian cells (FIG. 4g; and not shown).

Figure 5A:
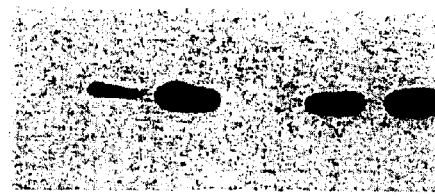

Phosphorylation at Ser133 in CREB and Ser117 in CREM is critical for activation and CBP interaction[17-21]. As ACT bypasses the CBP requirement (FIG. 4), we wondered whether a Ser>Ala substitution may prevent ACT function. The Ser>Ala117 mutation did not affect the CREM-ACT physical association tested by co-immunoprecipitation after transfection in mammalian cells (FIG. 5a). Strikingly, the Ser>Ala117 mutation did not decrease the stimulating ACT function, both in yeast and mammalian cells (FIGS. 5b, c). Analogous results were obtained with a CREB Ser>Ala133 mutation (not shown). Thus, ACT bypasses the phosphorylation requirement for activation.

Remarkable modulations in gene expression underlie the dramatic changes occuring during germ cells differentiation[3]. Unlike CBP, p300 and hTAF130, which are ubiquitous, ACT shows a stringent tissue-specific and temporal expression coordinated with CREM. Interactions between LIM-only proteins and transcription factors have been described in some differentiating cell systems[8, 22-25]. Here we provide the first evidence that LIM domains can bear an intrinsic activation potential. Moreover, ACT bypasses the classical requirement of activation by CREB and CREM. Indeed, a striking difference with CBP is that ACT association and function do not require phosphorylation at Ser117. The molecular mechanism by which ACT functions is intriguing. It is likely that ACT needs to interact with basal transcription factors or coactivators that must be conserved between yeast and mammalian cells. The absence of a CBP homolog in yeast demonstrates that ACT functions in a CBP-independent manner. Finally, the possible existence of other tissue-specific ACT-like molecules may suggest that ACT represents the first example of a novel class of co-activators whose function is specific of distinct steps of cellular differentiation programs.

So, the present invention deals with activator of CREM in Testis (ACT) having the formula: (SEQ ID NO:1)

1 MTSSQFDCQY CTSSLIGKKY VLKDDNLYCI SCY-DRIFSNY CEQCKEPIES

51 DSKDLCYKNR HWHEGCFRCN KCHHSLVEKP FVAKDDRLLC TDCYSNECSS

101 KCFHCKRTIM PGSRKMEFKG NYWHETCFVC EHCRQPIGTK PLISKESGNY

151 CVPCFEKEFA HYCNFCKKVI TSGGITFRDQ IWH-KECFLCS GCRKELYEEA

201 FMSKDDFPFC LDCYNHLYAK KCAACTKPIT GLRGAKFICF QDRQWHSECF

251 NCGKCSVSLV GEGFLTHNME ILCRKCGSGA DTDA or fragments thereof which are able to interact with CREM.

Said fragments or full-length ACT may be inserted within a protein, especially the active epitope of ACT may be inserted within protein to be used as marker of any other use. If it is used for imaging CREM the marker may be fluorescent or radioactive.

The present invention also deals with antibodies specific for the above protein which may be useful to interact with ACT or to prepare a diagnostic kit for identification of ACT in natural samples.

The invention also deals with DNA sequence coding the ACT protein, particularly the natural ACT DNA of FIG. 6.

Invention also deals with vectors expressing the above protein and cells comprising said vector and expressing the corresponding protein.

The expression vectors of the invention may require polynucleotide sequences which are necessary to effect the expression of coding sequences to which they are ligated to (i.e. the DNA sequence of the invention encoding for ACT or a fragment thereof). The nature of such control sequences differs depending upon the host organism; in eukaryotes, generally, such control sequences include promoter, enhancer, polyadenylation sequences and transcription termination sequence. The elements required for the expression are intended to include, at the minimum, all components whose presence is necessary for expression, and may also include additional components whose presence is advantageous. The vectors containing the nucleic acid sequence of interest can be transferred into the host cell by well-known methods, which vary depending on the type of the cellular host. For exemple, calcium phosphate, electroporation and lipofection may be used. These expression vectors are typically replicable in the host cells either as episomes or as integral part of the host chromosomal DNA. Host cells of the invention are chosen among bacterial cells, yeast cells, animal cells such as mammalian cells. In a preferred embodiment, the host cells are yeast cells.

An embodiment of the invention provides a method for selecting a compound or a compound likely to affect the interaction between the ACT protein or a fragment thereof and the CREM protein. This method of screening may be done in vitro with the corresponding proteins or in vivo, by using for example the two hybrid process, as described in the examples. In a preferred embodiment, this method is based on the two-hybrid assay . In this method, the compound of the invention is likely to interact with the protein ACT or a fragment thereof and/or to interact with the protein CREM or a fragment thereof, in order to form a complex likely to alter the transcriptional activity of genes which expression is regulated by ACT and/or CREM polypeptides. Said compound is likely to increase, decrease, modulate or void said transcriptional activity. In a preferred embodiment, the selected compound of the invention causes the transcriptional activity to decrease.

The method of the invention comprises the following steps:

a) providing a recombinant host cell containing a reporter gene, wherein the reporter gene expresses a detectable polypeptide when the reporter gene is activated by an amino acid sequence including a transcriptional activation domain, e.g., GAL4;

b) treating the host cell with a compound for which the capacity to alter the interaction between ACT protein or a fragment thereof and a CREM polypeptide is tested.

c) providing a chimeric ACT gene that is capable of being expressed in host cell, the chimeric ACT gene comprising a DNA sequence that encodes a ACT hybrid polypeptide, said ACT hybrid polypeptide comprising:
(i) the transcriptional activation domain; and
(ii) the ACT protein or a fragment thereof which is able to interact with CREM or a fragment thereof.

d) providing a CREM chimeric gene that is capable of being expressed in the host cell, the CREM chimeric gene comprising a DNA sequence that encodes a CREM hybrid polypeptide, the CREM hybrid polypeptide comprising:

(i) a DNA-binding domain, such as GAL4 that recognizes a binding site on the reporter gene in the host cell, and (ii) a CREM protein or a fragment thereof which are able to interact with the ACT proteins or fragments thereof.

Wherein interaction between the ACT hybrid polypeptide and the CREM hybrid polypeptide in the host cell under physiological conditions causes the transcriptional activation domain to activate transcription of the reporter gene.

e) introducing said chimeric ACT gene, said CREM chimeric gene and said compound into the host cell;

f) subjecting the host cells to conditions under which the ACT hybrid polypeptide and the CREM hybrid polypeptide are expressed in sufficient quantity for the reporter gene to be activated.

g) selecting the compound introduced into the host cell, that allows the reporter gene to be expressed to a degree lesser than its expression level in the absence of the said compound.

As used herein, the terms "interacting polypeptide sequence" refer to a portion of a ACT hybrid polypeptide which can form a specific binding interaction with a portion of a CREM hybrid polypeptide under suitable physiological conditions.

As used herein the term "physiological conditions" refers to temperature, pH, ionic strength, viscosity, and like biochemical parameters which are compatible with a viable organism, and/or which typically exist intracellularly in a viable cultured yeast cell or mamalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–2000 mM NaCl or KCl, pH 6.5–8.5, 20–45° C. and 0.01–10 mM divalent cation (e.g., Mg++, Ca++); preferably about 150 mM NaCl or KCl, pH 7.2–7.6, 5 mM divalent cation, and often include 0.01–1.0 percent nonspecific protein (e.g., BSA). Particular aqueous conditions may be selected by the practitioner according to conventional methods. For general guidance, the following buffered aqueous conditions may be applicable: 10–250 mM NaCl, 5–50 mM Tris HCl, pH 5–8 with optional addition of divalent cation(s) and/or metal chelators and/or nonionic detergents and/or membrane fractions.

According to a preferred embodiment, the reporter protein encoded by the reporter gene is expressed in control conditions (e.g., physiological conditions in the absence of agent) wherein the two hybrid proteins bind to each other and form a transcriptional activator that triggers or increases transcription of the reporter gene. Host organisms harboring such a two-hybrid system are cultured in the presence of said compound, and expression of the host organism reporter gene is determined and standardized to a parallel blank culture which lacks said compound. Compounds which produce a significant decrease in expression of the reporter gene in a host organism after a suitable time period (e.g., usually at least 1 hour, often at least 3 hours, preferably about 6 hours, occasionally overnight or longer) are thereby identified as inhibitors for blocking the intermolecular association between the ACT and CREM polypeptides.

For example and without limitation, suitable detectable genes are those which (1) confer a selectable phenotype to cells in which the detectable gene is efficiently expressed, and/or (2) encode a gene product (e.g., enzyme) which is conveniently detected such as by in situ assay or the like.

Suitable genes which confer a selectable phenotype are exemplified by, but not limited to, genes which complement auxotrophic mutations in a host organism (e.g., yeast HIS3), genes which encode drug resistance (e.g., $neo^R$), genes which induce cell proliferation, and other genes whose expression confers a selective growth advantage. Suitable genes which encode a gene product which is conveniently detected in situ are exemplified by, but not limited to, β-galactosidase (e.g. *E. coli* lacz), luciferase, alkaline, phosphatase, horseradish peroxidase, and the like.

In a preferred embodiment of method of the invention, yeast cells are the host organism, the detectable gene encodes β-galactosidase and/or a protein that complements an auxotrophic mutant yeast host cell, and the ACT and CREM hybrid polypeptides each comprise a binding domain derived from a signal transduction protein.

The compound tested and selected by the method of the invention include, but is not limited to, a chemical compound, a mixture of chemical compounds, a biological macromolecule such as a polypeptide, oligonucleotide, small biological molecule, (typical MW<5,000, preferably <1,000), and extract made from biological material such as bacteria, plants, fungi or animal (particularly mammalian) cells or tissues.

In a preferred embodiment, compounds are evaluated for potential activity as specific protein interaction inhibitors (that is to say an agent which selectively inhibits a binding interaction between ACT and CREM polypeptides but which does not substantially interfere with cell viability) by inclusion in screening assays described herein above. Compounds selected by the method of the invention, and which act as a ACT-CREM interaction inhibitors may have therapeutic potential as drugs for human use and/or may serve as commercial reagents for laboratory research or bioprocess control. Candidate drugs selected by the method of the invention are then tested further for activity in assays which are routinely used to predict suitability for use as human and veterinary drugs, including in vivo administration to non-human animals and often including administration to human in approved clinical trials.

In a preferred embodiment, ACT-CREM interaction inhibitors selected by the method of the invention are human or animal drugs useful to control male fertility. The drug of the invention can be administered orally, rectally, parenterally, or by local route, particularly for a man, for exemple by percutaneous route, or by injection, in particular subcutaneous, in the veterinary field. They can be in the form of tablets, dragees, capsules, granules, suppositories, injectable preparations, pressaries, creams, gels, microspheres, implants and patches prepared by the usual methods. Examples of suitable excipients are talc, gum arabic, lactose, starch, magnesium, stearate, cocoa butter, aqueous or non aqueous vehicle, fatty substances of animal or vegetable origin, paraffin derivatives, glycols, or emulsifying agents and preservatives.

In a preferred embodiment, the drug of the invention is biodegradable such that its potential activity as specific inhibitor is effective for a definite time in the organism. Accordingly, suitable excipients are used to modulate in vivo half-live of the drug of the invention.

It is also possible to use ACT, ACT-like compounds (for example proteins) or compound selected by the above-mentionned method, with a potential activity as ACT-CREM interaction activators to stimulate the CREM transcriptional activity in Testis.

Finally, the present invention deals with pharmaceutical composition comprising at least one of the above proteins or compounds or vectors expressing ACT or ACT-like compounds.

Another approach can be envisionned to control male fertility. This method is based on an immunological response to ACT using for exemple the antibodies of the invention.

The following examples will help to understand the above invention.

FIGURE LEGENDS

FIG. 1 Isolation of a CREM co-activator in testis by yeast two-hybrid assay. a) Gal4-DBD/CREM fusion used as bait and the CREM AD structure. Q1 and Q2 are glutamine-rich domains[27]. b) β-galactosidase levels in yeast expressing ACT and Gal4-DBD/CREM bearing the Gal1 upstream activation (UAS)-lacZ reporter. c) Selective medium growth of transformants coexpressing CREM and ACT. CREM corresponds to Gal4-DBD/CREM-AD; ACT indicates the clone obtained from the screening. Lamin (LAM), Gal4-DBD and Gal4-AD were negative controls. Individual Leu+ Trp+ transformants were streaked on synthetic medium lacking leucine and tryptophan (+HIS) or leucine, tryptophan, histidine (−HIS). d) ACT sequence (SEQ ID NO:1) with boxed LIM domains and schematic representation of ACT structure.

FIG. 2 Analysis of ACT expression. a) ACT is testis-specific. 10 μg of total RNA from mouse tissues analysed by RNAse protection assay. C indicates the mouse β-actin internal control. b) Western using CREM and ACT specific antibodies with purified testis cells. c)In situ hybridization of ACT mRNA expression in adult mouse testis. d) ACT is nuclear in spermatids. Immunohistological analysis of ACT protein in adult mouse testis (400×) and higher magnification (1000×).

FIG. 3 ACT associates with CREM. a) ACT binds to the AD. Scheme of CREM isoforms[12]. CREM proteins incubated with GST-ACT or GST were analyzed after GST pull-down by western using CREM antibodies. CREM proteins aliquots were quantitated by western. b) The third LIM domain is necessary for CREM association. ACT deletions used in GST pull-down; black boxes indicate LIM domains. Equal amounts of truncated proteins (GST-ACT fusions) or GST were incubated with CREM□. Blots were probed with CREM antibodies. c) ACT coimmunoprecipitates with CREM after transfection in COS cells of CREM and Myc-ACT expression vectors. Immunoprecipitates with CREM and Myc antibodies revealed by western with the reciprocal antibody. d) Coimmunoprecipitation of the CREM-ACT complex from testis extracts using the ACT antibody. Bracket indicates CREM proteins, asterisk heavy-chain immunoglobulin.

FIG. 4 ACT is a co-activator. a) ACT indicates the clone from the two-hybrid screen; ACT/Gal4-AD contains ACT in frame with Gal4-AD; ACT/Gal4-DBD contains ACT in frame with Gal4-DBD. In ACT(delGal4-AD) the Gal4-AD is deleted. Cotransformations in yeast with Gal4-DBD/CREM. Activity is reported as ratio between CREM values with or without ACT. For ACT/Gal4-DBD activity is compared to Gal4-DBD. b) Two-hybrid assay using G4DBD/CREM isoforms (FIG. 3a) fusions as baits and ACT. Activity is the ratio between the value of CREM isoforms with or without ACT. c) COS cells transfected with 0.25 μg of G4CAT[12] and G4CREM with or without pSVPKA[11] (0.5 μg), with increasing ACT amounts. CAT values in absence of ACT is 1. d) ACT induces the activity of a reporter containing two tandem somatostatin CREs[11] in COS cells at levels comparable to pSVPKA coexpression. e) Testis-specific ACE and calspermin[14,15] promoters are activated by ACT in COS cells. f) ACT is an activator. G4CAT transfected in COS cells with G4DBD-ACT. Activity without G4DBD-ACT is 1. g) ACT potentiates CREB-mediated activation. COS cells transfected with G4CAT (0.25 μg) and G4CREB, with increasing amounts of ACT.

Figure 5A:
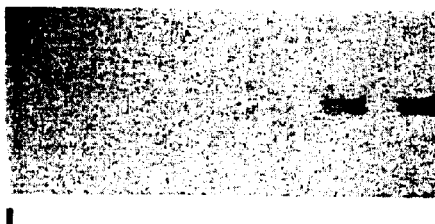

FIG. 5 CREM Ser117 phosphorylation is not required for ACT function. a) ACT interaction with CREM117. COS cells transfected with G4CREM or G4CREM117, with or without Myc-ACT. Immunoprecipitation was with Gal4-DBD antibodies; western was with CREM and Myc antibodies. b) ACT stimulates CREM independently of Ser117 in yeast. CREM Ser>Ala117 mutated fused to Gal4-DBD was expressed with or without ACT, and compared to CREM AD. c) ACT stimulates CREM117 in mammalian cells. COS cells transfected with 0.25 μg of G4CAT, G4CREM or G4CREM117, and increasing ACT amounts.

METHODS

Yeasts

The CREM AD (aa 1–229) and different fragments of CREM corrsponding to functional domains (CREMτ1 aa1–166; CREMτ2 aa1–38/88–229; CREMβ aa1–38/88–166; CREMQ1 aa39–87 ; CREMQ2 aa168–229) were obtained by PCR and cloned adjacent to Gal4-DBD into pGBT9 (Clontech). The CREB AD from pG4CREBΔLZ[26] was cloned in-frame with the Gal4-DBD in pGBT9.

A murine adult testis cDNA library (Clontech) was cotransformed with the pGBT9-CREM bait plasmid in CG1945 yeast cells. Yeast two-hybrid screening was performed as described (Clontech Matchmaker Two-Hybrid System Protocol). β-galactosidase assay was performed in Y190 yeast cells following the directions of the manufacturer. The results reported are in Miller units and are the means of measurements performed in triplicate from four independent transformations.

Antibodies and Western Analysis

Rabbit anti-ACT antiserum was prepared by sequential immunization with 100 μg of a peptide spanning aa 106–127 of the ACT protein, coupled to keyhole limpet hemocyanin (Pierce). ACT antibodies were purified by an affinity resin containing the same peptide immobilized onto a Sulfolink coupling gel (Pierce). Testis and purified germ cell protein extracts were prepared as previously described[10]. Purified ACT antibodies were used at a dilution of 1:2000. Immunocomplexes were detected by enhanced chemioluminescence (Pierce).

RNA Analysis

Total RNA was prepared and analyzed by RNase protection as previously described[27, 28]. The ACT RNA probe (internal fragment from +702 to +1072 into pBluescript SK−) was prepared using an in vitro transcription kit (Promega). CREM expression was scored using pN6/1[28]. In all analyses tRNA was used as a control for nonspecific protection. We scored for mouse β-actin expression as internal control for equal RNA loading.

Cell Lines and Transfections

COS cells (in DMEM, 5% FCS) were plated at a density of 5·10⁵/6 cm plate and transfected by the calcium phosphate co-precipitation technique. Total amount of transfected DNA was kept constant (10 μg) by adding pSG5 and pBluescript as necessary. Transfection efficiency was monitored by β-galactosidase assays using the CMVβ-gal plasmid. The pG5E4CAT[13], ACE[14] and calspermin[15] reporters have been described. The expression vectors for ACT, CREM, CREB and the catalytic subunit of PKA are based on pSG5[29]. G4CREM and pG4CREM117 plasmids have been described[12]. Data shown are means of three independent transfections, with inter-experimental variation less than 10%.

Recombinant Proteins

To construct GST-ACT fusion proteins, ACT and different deletions (ACT aa1–40; ACT aa1–101; ACT aa1–162; ACT aa1–221; ACT aa38–284) were obtained by PCR and subcloned in pGex-1λT (Pharmacia). GST fusions were expressed in E.Coli, extracted in BCO (20 mM Tris-HCl, pH8.0, 0.5 mM EDTA, 20% glycerol, 1 mM DTT and 0.5 mM PMSF) containing 500 mM KCl and 1% NP-40 and purified on glutathione-Sepharose resin (Pharmacia) . 20 µl of GST-protein beads (about 0.5 µg of proteins) were incubated with 100 ng of recombinant CREM isoforms at 4° C. for 30 min in 500 µl of BC0 buffer, 200 mM KCl and 0.2% NP-40. Beads were washed and bound proteins were eluted with 20 µl of SDS loading buffer.

Co-immunoprecipation Assays

Myc-ACT was constructed by inserting ACT in-frame with Myc epitopes into pCS2Myc[30]. COS cells were transfected with 5 µg of each plasmid and harvested in 1 ml of EBC (50 mM Tris-HCl pH8.0, 170 mM NaCl, 0.5% NP-40, 50 mM NaF) containing 1 mM PMSF and 10 µg/ml of aprotinin and leupeptin. Following preclearing for 30 min with 50 µl of a 1:1 slurry of protein A-Sepharose (Pharmacia), supernatants were incubated at 4° C. for 3 hrs with CREM antisera, anti-Myc 9E12 monoclonal antibody or anti GAL4-DBD (Santa Cruz) crosslinked to protein A-Sepharose. Beads were washed in NETN (10 mM Tris-HCl pH8.0, 250 mM NaCl, 5 mM EDTA, 0.5% NP-40) and resuspended in 20 µl of SDS loading buffer for the analysis.

Co-immunoprecipitation of the CREM-ACT complex from testis extract was performed using 4-week old mice. Extracts were prepared in EBC and immunoprecipitation (FIG. 3d) was performed with the anti-ACT antibody.

In Situ Hybridization and Immunocytochemistry

In situ hybridization was as described[10]. ACT antisense riboprobe was prepared by in vitro transcription (Promega). For control of non-specific signal, consecutive sections were hybridized with ACT sense RNA probe. Immunocytochemical analysis was as described[10]. Purified ACT antibodies were used at 1:500 dilution. The secondary antibody (CY3-conjugated antirabbit serum; Jackson) was used at 1:1000 dilution.

REFERENCES

1. Montminy, M. (1997). Transcriptional regulation by cyclic AMP. Annu. Rev. Biochem. 66, 807–822.
2. Sassone-Corsi P. (1995). Transcription factors responsive to cAMP. Annu. Rev.Cell Dev. Biol. 11, 355–377.
3. Sassone-Corsi, P. (1997). Transcriptional checkpoints determining the fate of male germ cells. Cell 88, 163–166.
4. Foulkes, N. S., Mellström, B., Benusiglio, E. & Sassone-Corsi, P. (1992). Developmental switch of CREM function during spermatogenesis from antagonist to activator. Nature 355, 80–84.
5. Ferreri, K., Gill, G. & Montminy, M. (1994). The cAMP-regulated transcription factor CREB interacts with a component of the TFIID complex. Proc. Natl. Acad. Sci. U S A 91, 1210–1213.
6. Nantel, F., Monaco, L., Foulkes, N. S., Masquilier, D., LeMeur M., Henriksen, K., Dierich, A., Parvinen, M. & Sassone-Corsi, P. (1996). Spermiogenesis deficiency and germ-cell apoptosis in CREM-mutant mice. Nature 380, 159–162.
7. Blendy, J. A., Kaestner, K. H., Weinbauer, G. F., Nieschlag, E. & Schutz, G. (1996) Severe impairment of spermatogenesis in mice lacking the CREM gene. Nature 380,162–165.
8. Dawid, I. B., Breen, J. J. & Toyama, R. (1998). LIM domains: multiple roles as adapters and functional modifiers in protein interactions. Trends Genet. 14, 156–162.
9. Curtiss, J. & Heilig, J. S. (1998). DeLIMiting development. BioEssays 20, 58–69.
10. Delmas, V., van der Hoorn, F., Mellstrom, B., Jegou, B. & Sassone-Corsi, P. (1993). Induction of CREM activator proteins in spermatids: down-stream targets and implications for haploid germ cell differentiation. Mol. Endocrinol. 7, 1502–1514.
11. Molina, C. A., Foulkes, N. S., Lalli, E. & Sassone-Corsi P. (1993). Inducibility and negative autoregulation of CREM: an alternative promoter directs the expression of ICER, an early response repressor. Cell 75, 875–886.
12. Laoide, B. M., Foulkes, N. S., Schlotter, F.& Sassone-Corsi, P. (1993). The functional versatility of CREM is determined by its modular structure. EMBO J. 12, 1179–1191.
13. Martinez-Balbas, M. A., Bannister, A. J., Martin, K., Haus-Seuffert, P., Meisterernst, M. & Kouzarides, T. (1998) The acetyltransferase activity of CBP stimulates transcription. EMBO J. 17, 2886–2893.
14. Zhou, Y., Sun, Z., Means, A. R., Sassone-Corsi, P. & Bernstein, K. E. (1996) CREM□ is a positive regulator of testis ACE transcription. Proc. Natl. Acad. Sci. USA 93, 12262–12266.
15. Sun, Z., Sassone-Corsi, P. & Means, A. R. (1995) Calspermin gene transcription is regulated by two cyclic AMP response elements contained in an alternative promoter in the Calmodulin Kinase IV gene. Mol. Cell. Biol. 15, 561–571.
16. Kunzler, M., Braus, G. H., Georgiev, O., Seipel, K. & Schaffner, W. (1994) Functional differences between mammalian transcription activation domains at the yeast GAL1 promoter. EMBO J. 13, 641–645.
17. Chrivia, J. C., Kwok, R. P. S., Lamb, N., Haniwawa, M., Montminy, M. R. & Goodman, R. H. (1993). Phosphorylated CREB binds specifically to the nuclear protein CBP. Nature 365, 855–859.
18. Kwok, R. P., Lundblad, J. R., Chrivia, J. C., Richards, J. P., Bachinger, H. P., Brennan, R. G., Roberts, S. G., Green, M. R. & Goodman, R. H. (1994). Nuclear protein CBP is a coactivator for the transcription factor CREB. Nature 370, 223–226.
19. Arias, J., Alberts, A. S., Brindle, P., Claret, F., Smeal, T., Karin, M., Feramisco, J. & Montminy, M. (1994) Activation of cAMP and mitogen responsive genes relies on a common nuclear factor. Nature 370, 226–229.
20. de Groot, R. P., den Hertog, J., Vandenheede, J. R., Goris, J. & Sassone-Corsi P. (1993) Multiple and cooperative phosphorylation events regulate the CREM activator function. EMBO J. 12, 3903–3911.
21. Gonzalez, G. A., & Montminy M. R. (1989). Cyclic AMP stimulates somatostatin gene transcription by phosphorylation of CREB at Ser 133. Cell 59, 675–680.
22. Valge-Archer, V. E., Osada, H., Warren, A. J., Forster, A., Li, J., Baer, R. & Rabbitts, T. H. (1994). The LIM protein RBTN2 and the basic helix-loop-helix protein TAL1 are present in a complex in erythroid cells. Proc. Natl. Acad. Sci. USA 91, 8617–8621.
23. Wadman, I., Li J., Bash, R. O., Forster, A., Osada, H., Rabbitts T. H. & Baer. R. Specific in vivo association between the bHLH and LIM proteins implicated in human T cell leukemia. (1994). EMBO J. 13, 4831–4839.
24. Osada, H., Grutz, G., Axelson, H., Forster, A. & Rabbitts, T. H. (1995). Association of erythroid transcription factors: complexes involving the LIM protein RBTN2 and the zinc-finger protein GATA1. Proc. Natl. Acad. Sci. USA 92, 9585–9589.
25. Kong, Y., Flick, M. J., Kudla, A. J. & Konieczny, S. F. (1997). Muscle LIM protein promotes myogenesis by enhancing the activity of MyoD. Mol. Cell. Biol. 17, 4750–4760.
26. Sheng, M., Thompson, M. A. & Greenberg M. E. (1991). CREB: a $Ca^{2+}$-regulated transcription factor phosphorylated by calmodulin-dependent kinases.Science 252, 1427–1430.

27. Chomczynski, P. & Sacchi, N. (1987). Single-step method of RNA isolation by acid guanidinium thiocyanate-phenol-chloroform extraction. Anal. Biochem. 162, 156–159.
28. Foulkes, N. S., Borrelli, E. & Sassone-Corsi, P. (1991). CREM gene: use of alternative DNA-binding domains generates multiple antagonists of cAMP-induced transcription. Cell 64, 739–749.
29. Green, S., Issemann, I. & Sheer, E. (1988). A versatile in vivo and in vitro eukaryotic expression vector for protein engineering. Nucleic Acids Res. 16, 369.
30. Rupp, R. A., Snider, L. & Weintraub H. (1994). Xenopus embryos regulate the nuclear localization of XMyoD. Genes Dev 8, 1311–1323.

What is claimed is:

1. An activator of CREM in Testis (ACT) having the sequence:

1 MTSSQFDCQY CTSSLIGKKY VLKDDNLYCI SCYDRIFSNY CEQCKEPIES

51 DSKDLCYKNR HWHEGCFRCN KCHHSLVEKP FVAKDDRLLC TDCYSNECSS

101 KCFHCKRTIM PGSRKMEFKG NYWHETCFVC EHCRQPIGTK PLISKESGNY

151 CVPCFEKEFA HYCNFCKKVI TSGGITFRDQ IWHKECFLCS GCRKELYEEA

201 FMSKDDFPFC LDCYNHLYAK KCAACTKPIT GLRGAKFICF QDRQWHSECF

251 NCGKCSVSLV GEGFLTHNME ILCRKCGSGA DTDA (SEQ ID NO: 1) or a fragment thereof that is able to interact with CREM.

2. A fusion polypeptide comprising the amino acid sequence set forth in SEQ ID NO:1, or a fragment of SEQ ID NO:1, wherein said fusion polypeptide is able to interact with CREM.

3. An isolated polynucleotide coding for a polypeptide with the amino acid sequence set forth in SEQ ID NO: 1, or a fragment of SEQ ID NO: 1, wherein said polypeptide is able to interact with CREM.

4. An isolated polynucleotide comprising a polynucleotide coding for a fusion polypeptide with the amino acid sequence set forth in SEQ ID NO:1, or a fragment of SEQ ID NO:1, wherein said fusion polypeptide is able to interact with CREM.

5. An isolated polynucleotide encoding a fusion polypeptide comprising the nucleotide sequence set forth in SEQ ID NO:2.

6. An expression vector comprising a polynucleotide coding for a polypeptide with the amino acid sequence set forth in SEQ ID NO: 1, or a fragment of SEQ ID NO: 1, wherein said polypeptide is able to interact with CREM.

7. An expression vector comprising a polynucleotide coding for a fusion polypeptide with the amino acid sequence set forth in SEQ ID NO:1, or a fragment of SEQ ID NO:1, wherein said fusion polypeptide is able to interact with CREM.

8. An expression vector comprising the nucleotide sequence of claim 5.

9. A cell comprising the expression vector of claim 6.

10. A cell comprising the expression vector of claim 7.

11. A cell comprising the expression vector of claim 8.

* * * * *

SEQUENCE LISTING

<160> NUMBER OF SEQ ID NOS: 2

<210> SEQ ID NO 1
<211> LENGTH: 1078
<212> TYPE: DNA
<213> ORGANISM: Murine adult testis
<220> FEATURE:
<221> NAME/KEY: CDS
<222> LOCATION: (130)..(981)

<400> SEQUENCE: 1

```
atcctgagtt attttcttca aagccaacac tactcagagt tctcaaattt cccaagaaag        60
aactgaagag tggcaacaaa gaacacttca tccgctgctc tacaaagaac tccaaaggat       120 aaaactgaa atg aca agt agt caa ttt gat tgt caa tac tgc act tca tcc       171
            Met Thr Ser Ser Gln Phe Asp Cys Gln Tyr Cys Thr Ser Ser
             1               5                  10 ctg att ggg aag aaa tat gta ctc aag gat gat aat cta tac tgc atc        219
Leu Ile Gly Lys Lys Tyr Val Leu Lys Asp Asp Asn Leu Tyr Cys Ile
 15                  20                  25                  30 tcc tgc tac gat cgt atc ttt tct aac tat tgt gag cag tgt aaa gaa        267
Ser Cys Tyr Asp Arg Ile Phe Ser Asn Tyr Cys Glu Gln Cys Lys Glu
                 35                  40                  45 cca att gaa tca gat tct aag gat ctt tgc tac aaa aac cgt cac tgg        315
Pro Ile Glu Ser Asp Ser Lys Asp Leu Cys Tyr Lys Asn Arg His Trp
             50                  55                  60 cat gaa gga tgc ttc agg tgc aac aaa tgc cat cac tct ttg gtg gaa        363
His Glu Gly Cys Phe Arg Cys Asn Lys Cys His His Ser Leu Val Glu
         65                  70                  75 aag cct ttc gtt gcc aag gat gat cgc ctg ctg tgc aca gac tgc tat        411
Lys Pro Phe Val Ala Lys Asp Asp Arg Leu Leu Cys Thr Asp Cys Tyr
 80                  85                  90 tcc aac gag tgt tcc tcc aag tgc ttc cac tgc aag aga acc atc atg        459
Ser Asn Glu Cys Ser Ser Lys Cys Phe His Cys Lys Arg Thr Ile Met
 95                 100                 105                 110 cca ggt tct cgg aaa atg gaa ttt aag ggc aat tac tgg cat gaa acc        507
Pro Gly Ser Arg Lys Met Glu Phe Lys Gly Asn Tyr Trp His Glu Thr
                115                 120                 125 tgc ttt gtg tgt gag cac tgc cga cag cca ata gga acc aag cct ttg        555
Cys Phe Val Cys Glu His Cys Arg Gln Pro Ile Gly Thr Lys Pro Leu
            130                 135                 140 atc tcc aaa gag agt ggc aat tat tgt gtg cca tgt ttt gag aag gag        603
Ile Ser Lys Glu Ser Gly Asn Tyr Cys Val Pro Cys Phe Glu Lys Glu
        145                 150                 155 ttt gct cat tac tgc aac ttc tgt aag aag gtg ata act tcc ggt ggg        651
Phe Ala His Tyr Cys Asn Phe Cys Lys Lys Val Ile Thr Ser Gly Gly
            160                 165                 170 ata acc ttc cgt gat cag ata tgg cat aaa gag tgt ttt ctg tgc agc        699
Ile Thr Phe Arg Asp Gln Ile Trp His Lys Glu Cys Phe Leu Cys Ser
175                 180                 185                 190 ggc tgc agg aaa gag ctt tat gag gag gca ttt atg tca aag gat gat        747
```

-continued

```
Gly Cys Arg Lys Glu Leu Tyr Glu Glu Ala Phe Met Ser Lys Asp Asp
                195                 200                 205 ttc cca ttc tgc ctg gat tgc tac aac cat ctt tat gct aaa aag tgt        795
Phe Pro Phe Cys Leu Asp Cys Tyr Asn His Leu Tyr Ala Lys Lys Cys
        210                 215                 220 gca gcc tgc acc aaa ccc atc act ggc ctc aga ggt gcc aag ttc atc        843
Ala Ala Cys Thr Lys Pro Ile Thr Gly Leu Arg Gly Ala Lys Phe Ile
            225                 230                 235 tgc ttt caa gac cgc cag tgg cac agt gag tgc ttc aac tgc gga aag        891
Cys Phe Gln Asp Arg Gln Trp His Ser Glu Cys Phe Asn Cys Gly Lys
        240                 245                 250 tgc tcg gtc tcc ttg gtg ggt gaa gga ttc ttg acc cat aac atg gaa        939
Cys Ser Val Ser Leu Val Gly Glu Gly Phe Leu Thr His Asn Met Glu
255                 260                 265                 270 atc tta tgc cgc aag tgt ggc tcc ggg gca gac act gac gct                981
Ile Leu Cys Arg Lys Cys Gly Ser Gly Ala Asp Thr Asp Ala
                275                 280 tagaaagaga caagtctttc accatctgaa atctgctttg cccttgctct cactaaatct      1041
ggaacttagt ggtaaaaaaa aaaaaaaaaa aaaaaaa                               1078
```

<210> SEQ ID NO 2
<211> LENGTH: 284
<212> TYPE: PRT
<213> ORGANISM: Murine adult testis

<400> SEQUENCE: 2

```
Met Thr Ser Ser Gln Phe Asp Cys Gln Tyr Cys Thr Ser Ser Leu Ile
1               5                   10                  15

Gly Lys Lys Tyr Val Leu Lys Asp Asp Asn Leu Tyr Cys Ile Ser Cys
                20                  25                  30

Tyr Asp Arg Ile Phe Ser Asn Tyr Cys Glu Gln Cys Lys Glu Pro Ile
            35                  40                  45

Glu Ser Asp Ser Lys Asp Leu Cys Tyr Lys Asn Arg His Trp His Glu
        50                  55                  60

Gly Cys Phe Arg Cys Asn Lys Cys His Ser Leu Val Glu Lys Pro
65                  70                  75                  80

Phe Val Ala Lys Asp Asp Arg Leu Leu Cys Thr Asp Cys Tyr Ser Asn
                85                  90                  95

Glu Cys Ser Ser Lys Cys Phe His Cys Lys Arg Thr Ile Met Pro Gly
            100                 105                 110

Ser Arg Lys Met Glu Phe Lys Gly Asn Tyr Trp His Glu Thr Cys Phe
        115                 120                 125

Val Cys Glu His Cys Arg Gln Pro Ile Gly Thr Lys Pro Leu Ile Ser
    130                 135                 140

Lys Glu Ser Gly Asn Tyr Cys Val Pro Cys Phe Glu Lys Glu Phe Ala
145                 150                 155                 160

His Tyr Cys Asn Phe Cys Lys Lys Val Ile Thr Ser Gly Gly Ile Thr
                165                 170                 175

Phe Arg Asp Gln Ile Trp His Lys Glu Cys Phe Leu Cys Ser Gly Cys
            180                 185                 190

Arg Lys Glu Leu Tyr Glu Glu Ala Phe Met Ser Lys Asp Asp Phe Pro
        195                 200                 205

Phe Cys Leu Asp Cys Tyr Asn His Leu Tyr Ala Lys Lys Cys Ala Ala
    210                 215                 220

Cys Thr Lys Pro Ile Thr Gly Leu Arg Gly Ala Lys Phe Ile Cys Phe
225                 230                 235                 240
```

```
Gln Asp Arg Gln Trp His Ser Glu Cys Phe Asn Cys Gly Lys Cys Ser
                245                 250                 255
Val Ser Leu Val Gly Glu Gly Phe Leu Thr His Asn Met Glu Ile Leu
                260                 265                 270
Cys Arg Lys Cys Gly Ser Gly Ala Asp Thr Asp Ala
            275             280
```